United States Patent [19]
Scherberich

[11] 3,954,783
[45] May 4, 1976

[54] RESOLUTION PROCESS AND SALT OF PROTECTED D-PENICILLAMINE AND L-PSEUDONOREPHEDRINE

[75] Inventor: Paul Scherberich, Neu Isenburg, Germany

[73] Assignee: Deutsche Gold- und Silber-Scheideanstalt vormals Roessler, Frankfurt, Germany

[22] Filed: Jan. 25, 1974

[21] Appl. No.: 436,787

[30] Foreign Application Priority Data
Jan. 27, 1973 Germany............................ 2304055

[52] U.S. Cl..................... 260/306.7 C; 260/501.12
[51] Int. Cl.²........................................ C07D 277/06
[58] Field of Search................. 260/306.7 C, 534 S, 260/501.12

[56] References Cited
UNITED STATES PATENTS

| | | | |
|---|---|---|---|
| 2,450,784 | 10/1948 | Duffin et al.................. | 260/306.7 C |
| 2,539,854 | 1/1951 | Mozingo et al................. | 260/534 S |

FOREIGN PATENTS OR APPLICATIONS

| | | | |
|---|---|---|---|
| 7,203,486 | 1/1973 | South Africa................ | 260/306.7 C |

*Primary Examiner*—R. J. Gallagher
*Attorney, Agent, or Firm*—Cushman, Darby & Cushman

[57] ABSTRACT

D,L-penicillamine is converted to D-penicillamine with the aid of 1-pseudonorephedrine.

29 Claims, No Drawings

RESOLUTION PROCESS AND SALT OF PROTECTED D-PENICILLAMINE AND L-PSEUDONOREPHEDRINE

The aminoacid D-penicillamine is known to be an important medicine for the treatment of Morbus Wilson, defective schizophrenia, scleroderma, cystinuria and chronic aggressive hepatitis as well as basic therapy of primary chronic polyarthritis. D-penicillamine is also useful as an antidote for heavy metal intoxications. Therapeutic uses are only found for D-penicillamine since the L-isomer is much more toxic.

It is known to recover D-penicillamine in an expensive, hydrolytic process from the very expensive starting material penicillin. The D-penicillamine produced in this way is so expensive that it cannot be used for broad medicinal purposes, especially as a basic therapeutic for long lasting treatment of primary chronic polyarthritis. For this reason a total synthesis of D-penicillamine is of special significance.

It is also known, however, to produce D,L-penicillamine synthetically and to recover the D-penicillamine by splitting the racemate. As optically active bases for this purpose there have been used d-pseudoephedrine and l-ephedrine (see "The Chemistry of Penicilline" (1949) Princeton University Press; British Pat. No. 585,413 and corresponding Duffin U.S. Pat. No. 2,450,784 and Belgian Pat. No. 738,520).

For the racemate splitting the D,L-penicillamine must be converted into suitable derivatives, that is, protective groups must be introduced into the penicillamine molecule, as is customary in the racemate splitting of amino acids. Suitable derivatives for the racemate splitting for example are the N-acylated products of D,L-penicillamine or of S-benzyl-D,L-penicillamine as well as the acylation product of the reaction product of D,L-penicillamine with carbonyl compounds.

These processes for the racemate splitting of D,L-penicillamine, however, are only slightly satisfactory since in the reaction of the D,L-penicillamine derivatives with the above named splitting bases the undesired salt of the L-penicillamine derivative and the optically active base precipitates. It is known, however, that in principle the antipode crystallizing out of the reaction mixture has the higher purity (H. D. Jakubke and H. Jeschkeit, "Aminosaeuren, Peptide, Proteine", Akademie-Verlag, Berlin, 1969, as well as L. F. Fieser and M. Fieser, "Lehrbuch der Organischen Chemie", Verlag Chemie, Weinheim, 1957).

It has now been found that it is especially advantageous to use l-pseudonorephedrine of the formula

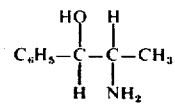

as the optically active base for the recovery of D-penicillamine from D,L-penicillamine. The splitting of the racemate of D,L-penicillamine proceeds with the help of this optically active base with very high yields. The D-penicillamine is obtained in high purity since the desired salt of the D-acid and the l-base is the very much more difficultly soluble and precipitates.

The l-pseudonorephedrine can be added as either the free base or as a salt thereof. As salts of l-pseudonorephedrine there are chiefly used salts with organic acids, preferably with sulfonic acids or more preferably with carboxylic acids. As sulfonic acids there can be used for example aliphatic sulfonic acids, e.g., alkane sulfonic acids, such as methane sulfonic acid, methane trisulfonic acid, propan-2-sulfonic acid, ethanesulfonic acid, butan-1-sulfonic acid, propan-1-sulfonic acid, hexane-1-sulfonic acid, dodecane-1-sulfonic acid or aromatic sulfonic acids such as p-toluenesulfonic acid and especially benzene sulfonic acid. As carboxylic acids there can be used saturated or unsaturated carboxylic acids which are unsubstituted or have an —OH, —NH₂, —NHR, —NR₂, —OR, —SN, —SR or halogen substituent. There can be used aliphatic mono or polycarboxylic acids, e.g., alkanoic acids, such as isobutyric acid, n-valeric acid, acrylic acid, isovaleric acid, trimethyl acetic acid, lactic acid, oxalic acid, malonic acid, adipic acid, maleic acid, succinic acid, tartaric acid, citric acid, crotonic acid, especially those containing 1 to 6 carbon atoms, e.g., alkanoic acids such as formic acid, acetic acid, propionic acid, butyric acid or caproic acid, araliphatic carboxylic acids such as phenyl acetic acid, mandelic acid, cinnamic acid and especially 3-phenyl propionic acid or aromatic carboxylic acids, i.e., carbocyclic aromatic acids such as phthalic acid, terephthalic acid, salicylic acid and especially benzoic acid or heteroaromatic carboxylic acids such as thiophene-2-carboxylic acid, thiazole-4-carboxylic acid, furane-2-carboxylic acid, picolinic acid, or isonicotinic acid.

As in the known processes for racemate splitting also in the process of the present invention the D,L-penicillamine must first be converted into a suitable derivative for the racemate splitting before the reaction with the l-pseudonorephedrine can take place. At least one of the hydrogen atoms of the amino group must be protected. At the same time the hydrogen atom of the mercapto group can be protected. For the protection of the hydrogen atom or atoms there can be used any of the known methods, such as those described in "Chemistry of the Aminoacids", J. P. Greenstein and M. Winitz, J. Wiley and Sons, Inc., New York, 1961; as well as in Houben Weyl, 1958, Vol. 11, part 2, Georg Thieme Verlag. Such protection can be obtained for example if D,L-penicillamine is converted in known manner to a compound having the formula:

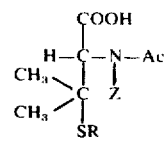

in which Ac is an acyl group, especially benzoyl, tosyl, nitrophenyl, sulfenyl, lower alkanoyl, e.g., acetyl or preferably formyl, Z is hydrogen or together with Ac can be a diacyl group, especially phthaloyl and R is hydrogen or benzyl or can have the same meaning as Ac. Examples of such compounds include D,L-N-formyl penicillamine, D,L-N-acetyl penicillamine, D,L-N-propionyl penicillamine, D,L-N-benzoyl penicillamine, D,L-N-tosyl penicillamine, D,L-nitrophenyl sulfenyl penicillamine, D,L-N-phthaloyl penicillamine, D,L-N-formyl-S-benzyl penicillamine, D,L-N-acetyl-S-benzyl penicillamine, D,L-N-propionyl-S-benzyl penicillamine, D,L-N-benzoyl-S-benzyl penicillamine, D,L-N-tosyl-S-benzyl penicillamine, D,L-N-nitrophenylsulfenyl-S-benzyl penicillamine, D,L-N-phthaloyl-S-benzyl penicillamine, D,L-N-formyl-S-formyl penicillamine, D,L-N-formyl-S-acetyl penicillamine, D,L-N-formyl-S-benzoyl penicillamine, D,L-N-formyl-S-tosyl penicillamine, D,L-N-formyl-S-nitrophenyl-sulfenyl penicillamine, D,L-N-phthaloyl-S-benzyl penicillamine, D,L-N-acetyl-S-formyl penicillamine, D,L-N-formyl-S-formyl penicillamine, D,L-N-phthaloyl-S-propionyl penicillamine, D,L-N-acetyl-S-benzoyl penicillamine, D,L-N-formyl-S-tosyl penicillamine, D,L-N-formyl-S-nitrophenyl-sulfenyl penicillamine.

Preferably, however, the protection of such groups is provided by converting the D,L-penicillamine in known manner into a thiazoline-4-carboxylic acid of the formula:

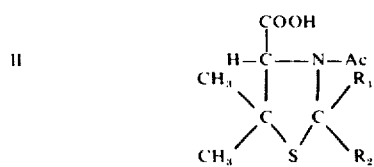

II in which $R_1$ and $R_2$ are the same or different and are hydrogen, alkyl of 1 to 8 carbon atoms, cycloalkyl with 5 to 8 carbon atoms or aryl, i.e., alkyl aryl or $R_1$ and $R_2$ together with the adjacent carbon atom from a cycloalkylene ring, e.g., of 5, 6, 7 or 8 carbon atoms and Ac is an acyl group, especially benzoyl, tosyl, nitrophenyl-sulfenyl, lower alkanoyl, e.g., acetyl or preferably formyl.

Of these protected compounds there are preferred those in which the D,L-penicillamine is converted into an N-acetyl or, preferably N-formyl derivative of a 2,2-dialkyl-5,5-dimethyl-thiazolidine-4-carboxylic acid. Of these there is preferred 3-formyl-2,2,5,5-tetramethyl-thiazolidine-4-carboxylic acid (N-formyl-isopropylidene-D,L-penicillamine)or 3-formyl-2,2-pentamethylene-5,5-dimethyl-thiazolidine-4-carboxylic acid. These thiazolidine-4-carboxylic acids can be made in a simple manner from D,L-penicillamine and the corresponding carboxylic compounds (The Chemistry of Penicilline (1949), Princeton University Press). The conversion into the N-acyl compounds as well as the compounds with protected mercapto groups is described in the same literature.

Other thiazolidine-4-carboxylic acids which can be used and which are within formula II include D,L-3-acetyl-2,2,5,5-tetramethyl-thiazolidine-4-carboxylic acid, D,L-3-propionyl-2,2,5,5-tetramethyl thiazolidine-4-carboxylic acid, D,L-3-benzoyl-2,2,5,5-tetramethyl-thiazolidine-4-carboxylic acid, D,L-3-p-toluenesulfenyl-2,2,5,5-tetramethyl-thiazolidine-4-carboxylic acid, D,L-3-p-nitrophenylsulfenyl-2,2,5,5-tetramethyl-thiazolidine-4-carboxylic acid, D,L-3-formyl-2,2-diethyl-5,5-dimethyl-thiazolidine-4-carboxylic acid, D,L-3-formyl-2,2-hexamethylene-5,5-dimethyl-thiazolidine-4-carboxylic acid, D,L-3-formyl-2,2-dioctyl-5,5-dimethyl-thiazolidine-4-carboxylic acid, D,L-3-formyl-2,2-dibutyl-5,5-dimethyl-thiazolidine-4-carboxylic acid, D,L-3-formyl-2,2-dicyclopentyl-5,5-dimethyl-thiazolidine-4-carboxylic acid, D,L-3-formyl-2,2-diphenyl-5,5-dimethyl-thiazolidine-4-carboxylic acid, D,L-3-formyl-2,2-di-o-tolyl-5,5-dimethyl-thiazolidine-4-carboxylic acid, D,L-3-acetyl-2,2-dihexyl-5,5-dimethyl-thiazolidine-4-carboxylic acid.

As solvents for the separation of the racemate there can be used water or more preferably organic solvents such as alcohols, halogenated aliphatic hydrocarbon, ethers, ketones, esters, aromatic hydrocarbons, etc. There are preferably used isopropanol and dioxane.

Specific examples of additionally suitable solvents include methanol, ethanol, butanol, isooctyl alcohol, isodecyl alcohol, dodecyl alcohol, benzene, toluene, chloroform, carbon tetrachloride, dichloroethylene, 1,1,2,2-tetrachloroethane, dibromoethylene, acetone, methyl ethyl ketone, methyl butyl ketone, diethyl ketone, ethyl formate, ethyl acetate, ethyl propionate, methyl formate, ethyl formate, ethyl propionate, ethyl butyrate, propyl acetate, ethyl propionate.

In the carrying out of the process of the invention there is first provided that the D,L-penicillamine is converted in known way to a suitable derivative (protected D,L-penicillamine) and this is dissolved in water or preferably in an organic solvent or mixture of organic solvents such as those set forth above, and this solution, in a given case with heating mixed with l-pseudonorephedrine or a salt thereof, in a given case dissolved in an organic solvent such as any of those set forth above. Frequently immediately or, under some conditions, only after long standing, in a given case at low temperatures and after inoculation the more difficulty soluble salt of the D-penicillamine derivative and l-pseudonorephedrine precipitates out while the diastereoisomeric salt, the optical antipode or the racemic mixture or mixtures thereof remain in the mother liquor. The difficultly soluble salt can be converted into the mineral acid salt of D-penicillamine in known manner, for example, by treatment with dilute mineral acid, e.g., hydrochloric acid, hydrobromic acid, sulfuric acid, nitric acid. The free D-penicillamine can be set free in known manner from the mineral acid salt, for example by treatment with a base, e.g., sodium hydroxide, potassium hydroxide, sodium acetate, sodium carbonate, potassium carbonate, amines, e.g., triethyl amine, tripropylamine, tributylamine, etc.

The process can be carried out in reverse and the solution of the L-norephedrine mixed with the derivative of the racemic penicillamine which preferably is dissolved in an organic solvent such as those set forth above for example.

The process of the invention is advantageously carried out using 0.1 to 3 moles, preferably 0.5 to 1.1 moles of l-pseudonorephedrine per mole of racemate. In all ranges the more difficultly soluble salt of the D-penicillamine derivative and l-pseudonorephedrine precipitates. This precipitation is nearly quantitative by employing approximately stoichiometric quantities of reactants. Using less than 0.5 mole of l-pseudonorephedrine there remains in the mother liquor the racemate and optical antipode; using per mole of racemate between 0.5 and < 1 mole of l-pseudonorephedrine the mother liquor still contains besides the optical antipodes diastereomer salt. If there is added per mole of racemate more than 1 mole of the optically active l-pseudonorephedrine there is still contained in the mother liquor in addition to the diastereomeric salt some l-pseudonorephedrine.

The salt of the penicillamine derivative and l-norephedrine accumulating in the reaction can be recovered in pure form in known manner because of its very favorable solubility relation, for example by filtration, evaporation of the mother liquor and purification by recrystallization.

In each case there precipitates first in the racemate splitting the more difficultly soluble salt of the D-penicillamine derivative and l-pseudonorephedrine while the other diastereomer remains in solution. This was completely surprising since in the use of both D-pseudoephedrine and l-ephedrine the salt of the L-penicillamine derivative and the splitting base is more difficultly soluble.

The splitting of the more difficultly soluble salt likewise occurs in known manner through treatment with preferably aqueous mineral acids, for example dilute hydrochloric acid (or any of the other mineral acids mentioned above), whereby first the splitting base (l-pseudonorephedrine) is recovered in the form of the mineral acid salt and the D-penicillamine derivative is obtained.

The splitting of the D-penicillamine derivative takes place in known manner by splitting off the protective group, for example debenzylation or acid hydrolysis.

In an analogous manner L-penicillamine can be recovered from the mother liquor of the splitting of the racemate. It is especially advantageous, however, to racemize the L-penicillamine derivative in known manner, in a given case recovered through mineral acid splitting of its salt with the optically active l-norephedrine, whereby it is possible to recycle the therapeutically nonusable L-penicillamine.

Unless otherwise indicated all parts and percentages are by weight.

In the following examples, the rotatory power of the materials is always given as specific rotation $[\alpha]_D^{20}$ in degrees . cm$^3$/dm . g.

EXAMPLE 1

1.9 kg (10 moles) of crude D,L-penicillamine hydrochloride was converted into 1.5 kg (6.9 moles) of D,L-3-formyl-2,2,5,5-tetramethyl-thiazolidine-4-carboxylic acid by reaction with acetone and subsequent formylation with a mixture of formic acid and acetic anhydride in the presence of sodium acetate. This substance was dissolved at 60° to 70° C. in 6 liters of n-butyl acetate. The solution was treated with 1.05 kg (7 moles) of l-pseudo-norephedrine and held at 80° to 90° C. for 30 minutes. The mixture was cooled to room temperature and stirred for an additional hour. Thereupon the salt of D-3-formyl-2,2,5,5-tetramethyl-thiazolidine-4-carboxylic acid and l-pseudonorephedrine precipitated. This was filtered off with suction, washed with 1 liter of n-butyl acetate and dried at about 50° C. under reduced pressure. The yield amounted to 0.94 kg, corresponding to 75%. The salt had a specific rotation of +26° and a melting point of 180° to 182° C.

The salt recovered was suspended at room temperature in 3 liters of water. The suspension was brought to a pH of about 1 with concentrated hydrochloric acid and then stirred for about 30 minutes at room temperature. The solid which separated was filtered off with suction, washed with 1 liter of water and dried at about 50° C. under reduced pressure. There were obtained 500 grams corresponding to a 92% yield of D-3-formyl-2,2,5,5-tetramethyl-thiazolidine-4-carboxylic acid. This had a specific rotation of +53° and a melting point of 182° to 183° C.

There was recovered from the mother liquor after addition of concentrated aqueous sodium hydroxide up to a strongly alkaline reaction several shakings with methylene chloride 340 grams of l-pseudonorephedrine, corresponding to 90%. This had a specific rotation of −31° and a melting point of 75° to 76° C.

500 grams of D-3-formyl-2,2,5,5-tetramethyl-thiazolidine-4-carboxylic acid was heated at reflux in a mixture of 2 liters of water and 1 liter of concentrated hydrochloric acid, whereby formic acid and acetone were continuously distilled off. After 2 hours the solution was evaporated to dryness under reduced pressure. There were recovered 430 grams of crude D-penicillamine hydrochloride. This was dissolved in 2 liters of 96% ethanol. The solution was adjusted to a pH value of about 6 to 7 with triethylamine, whereupon the free D-penicillamine precipitated. This was filtered off with suction, washed with alcohol and dried under reduced pressure at about 50° C. It had a specific rotation of −63° and a melting point of 202° to 204° C. The yield was 260 grams, corresponding to 75%.

EXAMPLE 2

The procedure was the same as in example 1 but there was used toluene as the solvent. From 43.5 grams (0.2 mole) of D,L-3-formyl-2,2,5,5-tetramethyl-thiazolidine-4-carboxylic acid and 30.2 grams (0.2 mole) of l-pseudonorephedrine there was obtained 26.5 grams of the salt of D-3-formyl-2,2,5,5-tetramethyl-thiazolidine-4-carboxylic acid and l-pseudonorephedrine, corresponding to a yield of 72%. This had a specific rotation of +25° and a melting point of 182° to 183° C. The working up of the salt to D-penicillamine took place according to example 1. There were recovered 6.5 grams of D-penicillamine. This had a specific rotation of −63° and a melting point of 202° to 205° C.

EXAMPLE 3

The procedure was the same as in example 1 except that there were used as starting materials 43.5 grams (0.2 mole) of D,L-3-formyl-2,2,5,5-tetramethyl-thiazolidine-4-carboxylic acid and 16.6 gram (0.11 mole) of l-pseudonorephedrine. As solvent there was used ethyl acetate. The salt of D-3-formyl-2,2,5,5-tetramethyl-thiazolidine-4-carboxylic acid and l-pseudonorephedrine recovered had a specific rotation of +25° and a melting point of 180° to 182° C. the yield was 28 grams, corresponding to 76%.

EXAMPLE 4

The procedure was the same as in example 1 but there were used as the starting materials 250 grams (1.0 mole) of D,L-3-formyl-2,2-pentamethylene-5,5-dimethyl-thiazolidine-4-carboxylic acid (produced by the condensation of D,L-penicillamine hydrochloride with cyclohexanone and subsequent formylation) and 75 grams (0.5 mole) of l-pseudonorephedrine. The salt of D-3-formyl-2,2-pentamethylene-5,5-dimethyl-thiazolidine-4-carboxylic acid and l-pseudonorephedrine recovered had a specific rotation of +30° and a melting point of 151° to 153° C. The yield was 145 grams, corresponding to 71%. The splitting of the salt took place according to example 1. There resulted 82 grams, corresponding to a 90% yield of D-3-formyl-2,2-pentamethylene-5,5-dimethylthiazolidine-4-carboxylic acid. This had a specific rotation of +63° C. and a melting point of 189° to 191° C.

EXAMPLE 5

43.5 grams (0.2 mole) of D,L-3-formyl-2,2,5,5-tetramethyl-thiazolidine-4-carboxylic acid were dissolved at 60° to 70° C. in 160 ml of n-butyl acetate. The solution was treated with stirring with 21.6 grams (0.11 mole) of l-pseudonorephedrine formate, held for 30 minutes at 80° to 90° C. and then cooled to room temperature. There were obtained 30 grams, corresponding to a 73% yield of the salt of D-3-formyl-2,2,5,5-tetramethyl-thiazolidine-4-carboxylic acid and l-pseudonorephedrine. This salt had a specific rotation of +25° and a melting point of 180° to 183° C.

EXAMPLE 6

The procedure of example 5 was repeated but starting with 43.5 grams (0.2 mole) of D,L-3-formyl-2,2,5,5-tetramethyl-thiazolidine-4-carboxylic acid and 42 grams (0.2 mole) of l-pseudonorephedrine acetate. The salt of D-3-formyl-2,2,5,5-tetramethyl-thiazolidine-4-carboxylic acid and l-pseudonorephedrine recovered had a specific rotation of +26° and a melting point of 180° to 183° C. The yield amounted to 28 grams, corresponding to 69%.

EXAMPLE 7

The procedure of example 5 was repeated but using as the starting materials 51.4 grams (0.2 mole) of D,L-3-formyl-2,2-pentamethylene-5,5-dimethyl-thiazolidine-4-carboxylic acid and 23 grams (0.05 mole) of l-psuedonorephedrine maleate. The salt of D-3-formyl-2,2-pentamethylene-5,5-dimethyl-thiazolidine-4-carboxylic acid and l-pseudonorephedrine recovered had a specific rotation of +29° and a melting point of 152° to 154° C. The yield amounted to 30 grams, corresponding to 73%.

EXAMPLE 8

The procedure of example 5 was repeated but there were used as starting materials 43.5 grams (0.2 mole) of D,L-3-formyl-2,2,5,5-tetramethyl-thiazolidine-4-carboxylic acid and 30 grams (0.1 mole) of l-pseudonorephedrine benzenesulfonate. The salt of D-3-formyl-2,2,5,5-tetramethyl-thiazolidine-4-carboxylic acid and l-pseudonorephedrine recovered had a specific rotation of +26° and a melting point of 182° to 183° C. The yield amounted to 29 grams, corresponding to 70%.

What is claimed is:

1. The optically active salt of a protected D-form of penicillamine and l-pseudonoresphedrine where the protected penicillamine has the formula

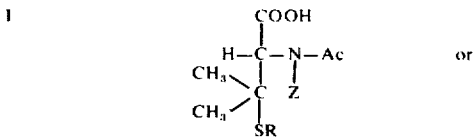

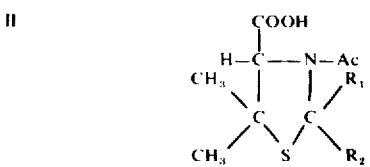

where Ac is benzoyl, tosyl, nitrophenyl-sulfenyl, formyl, acetyl or propionyl, R is hydrogen, benzyl or Ac, $R_1$ and $R_2$ are hydrogen, alkyl of 1 to 8 carbon atoms, cycloalkyl of 5 to 8 carbon atoms, phenyl or tolyl or $R_1$ and $R_2$ together with the adjacent carbon atoms of the thiazoline ring form a cycloalkylene ring of 5 to 8 carbon atoms and Z is hydrogen or together with Ac is phthaloyl.

2. The optically active salt according to claim 1 having formula II wherein Ac is acetyl or formyl and $R_1$ and R are each methyl or $R_1$ and $R_2$ together with the adjacent carbon atom are cyclopentamethylene.

3. A compound according to claim 1 having formula I.

4. A compound according to claim 3 wherein Ac is formyl, acetyl or propionyl and Z is hydrogen.

5. A compound according to claim 4 wherein Ac is formyl.

6. A compound according to claim 5 wherein R is benzyl.

7. A compound according to claim 1 having formula II.

8. A compound according to claim 7 wherein $R_1$ and $R_2$ are alkyl of 1 to 8 carbon atoms, cycloalkyl of 5 to 8 carbon atoms, phenyl or tolyl or $R_1$ and $R_2$ together with the adjacent carbon atom are cycloalkylene of 5 to 8 carbon atoms.

9. A compound according to claim 8 wherein Ac is formyl, acetyl or propionyl.

10. A compound according to claim 8 wherein Ac is formyl or acetyl and $R_1$ and $R_2$ are both alkyl.

11. A compound according to claim 10 wherein Ac is formyl.

12. A compound according to claim 11 wherein $R_1$ and $R_2$ are both methyl.

13. A compound according to claim 1 of formula II wherein $R_1$ and $R_2$ together with the adjacent carbon atom is cycloalkylene of 5 to 8 carbon atoms.

14. A compound according to claim 13 wherein Ac is formyl or acetyl and the cycloalkylene is cyclopentamethylene.

15. In a process of recovering the optically active salt of a protected D-form of penicillamine and an optically active base wherein the protected D-form of penicillamine has formula I or II according to claim 1 including the step of crystallizing out of solution in a solvent which comprises water, an alkanol, an aliphatic hydrocarbon, a halogenated aliphatic hydrocarbon, dioxane, a ketone, a carboxylic acid ester or an aromatic hydrocarbon of the salt of said protected penicillamine having formula I or II with an optically active base, the improvement comprising employing the D,L form of said protected penicillamine and l-pseudonorephedrine and preferentially precipitating the salt of the D form of said protected penicillamine of formula I or II with said l-pseudonorephedrine.

16. A process according to claim 15 wherein the protected penicillamine has formula II and $R_1$ and $R_2$ together with the adjacent carbon atom is cycloalkylene of 5 to 6 carbon atoms.

17. A process according to claim 16 wherein Ac is formyl and the cycloalkylene is cyclopentamethylene.

18. A process according to claim 15 wherein the solvent comprises an alkanol, an aliphatic hydrocarbon, halogenated aliphatic hydrocarbon, dioxane, a ketone, a carboxylic acid ester or an aromatic hydrocarbon.

19. A process according to claim 18 wherein the solvent is an alkanol of 1 to 3 carbon atoms or dioxane.

20. A process according to claim 15 wherein there is used 0.1 to 3 moles of l-pseudonorephedrine per mole of D,L-racemate of the protected penicillamine.

21. A process according to claim 20 wherein there is used 0.5 to 1.1 moles of l-pseudonorephedrine per mole of the D,L-racemate.

22. A process according to claim 15 wherein the protected penicillamine has formula I.

23. A process according to claim 22 wherein Ac is formyl or acetyl, Z is hydrogen and R is hydrogen or benzyl.

24. A process according to claim 15 wherein the protected penicillamine has formula II.

25. A process according to claim 24 wherein $R_1$ and $R_2$ are alkyl of 1 to 8 carbon atoms, cycloalkyl of 5 to 8 carbon atoms, phenyl or tolyl or $R_1$ and $R_2$ together with the adjacent carbon atom are cycloalkylene of 5 to 8 carbon atoms.

26. A process according to claim 25 wherein Ac is formyl or acetyl.

27. A process according to claim 26 wherein $R_1$ and $R_2$ are both alkyl.

28. A process according to claim 27 wherein Ac is formyl.

29. A process according to claim 28 wherein $R_1$ and $R_2$ are both methyl.

* * * * *